(12) United States Patent
Grimmer et al.

(10) Patent No.: US 6,699,911 B2
(45) Date of Patent: Mar. 2, 2004

(54) CATALYTIC REDUCTION OF ALKYNE COMPOUNDS

(75) Inventors: Johannes Grimmer, Ludwigshafen (DE); Thomas Müller, Dirmstein (DE); Hansgeorg Ernst, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 78 days.

(21) Appl. No.: 09/954,263

(22) Filed: Sep. 18, 2001

(65) Prior Publication Data

US 2002/0045768 A1 Apr. 18, 2002

(30) Foreign Application Priority Data

Sep. 28, 2000 (DE) .......................................... 100 49 271

(51) Int. Cl.$^7$ ...................... A61K 31/12; A61K 31/045; C07D 317/48; C07D 317/00; C07C 45/00

(52) U.S. Cl. ...................... 514/678; 514/464; 514/725; 514/728; 549/437; 549/434; 568/338; 568/347; 568/361

(58) Field of Search ................................ 549/437, 434; 568/338, 347, 361, 830; 514/678, 464, 725, 728

(56) References Cited

U.S. PATENT DOCUMENTS 5,455,362 A * 10/1995 Ernst et al. .................. 549/437
5,625,099 A *  4/1997 Ernst et al. .................. 568/347

FOREIGN PATENT DOCUMENTS

DE          4322277     *  1/1995
EP           120341     * 10/1984

OTHER PUBLICATIONS

Chemical Abstract DN 122:265715, also cited as DE 4322277 which is equivalent to U.S.P. 5455362.*
Chemical Abstract DN 112:98891, also cited as J. Chem. Soc., Chemical Communications, 12, 784–6(1989).*
McShane et al, Exo–methylenecephama via Zn/NH4CL', Syn. Comm. 16/6,649–52(1986); CAS ABS106:18193.*
Zhang et al,"Direct Syn.od PAP",Yangzhou Daxue Xuebao, Ziran Kexueban, 2/2,17–18,37(1999).*
Lu et al,"Improvement of electr.syn. of sorbitol",Zhejiang Gongye Daxue Xuebao, 26/3,263–266(1998).*
Larsen et al. J. Chem. Soc., Chemical Communications, 12, 784–6(1989), also cited as Chemical Abstract DN 112:98891.*

(List continued on next page.)

Primary Examiner—John M. Ford
Assistant Examiner—Sudhaker B Patel
(74) Attorney, Agent, or Firm—Keil & Weinkauf

(57) ABSTRACT

A process is provided for the preparation of cyclohexene derivatives of general formula I or II:

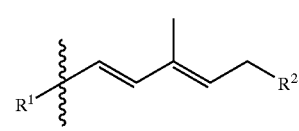

I

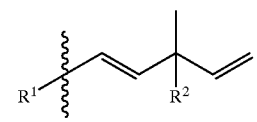

II in which the substituents $R^1$ and $R^2$ independently of one another are defined as follows:
$R^1$ is

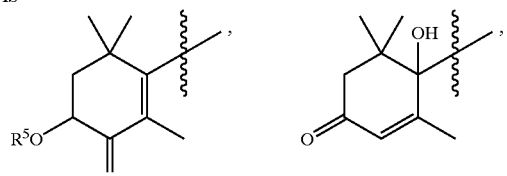

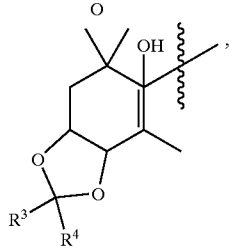

$R^2$ is OH or a protective group convertible to a hydroxyl group by hydrolysis;
$R^3$ and $R^4$
    are hydrogen or $C_1$–$C_4$-alkyl; and
$R^5$ is hydrogen or $C_1$–$C_4$-acyl,
by the reduction of alkyne compounds of general formula III or IV:

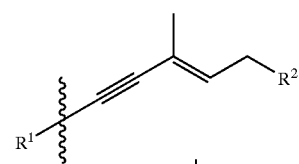

III

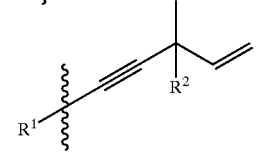

IV in which the substituents $R^1$ and X are as defined above, wherein the reducing agent used is a mixture of zinc and at least one compound B selected from the group consisting of ammonium salts, copper salts and alkali metal and alkaline earth metal salts.

7 Claims, No Drawings

OTHER PUBLICATIONS

Aerssens et al., *Synth. Comm.*, 20(22), 3421–25, 1990.
Boland et al., *Helv. Chim. Acta.*, vol. 70, 1025–40, 1987.
Souto et al., *Helv. Chim. Acta*, vol. 83, 2617–2628, 2000.
Morris et al. "Reduction with Zinc of Triple Bonds to cis Double Bonds in Long Chain Conjugated Fatty Acids" J. Am. Oil Chem. Soc. vol. 49 pp. 92–94.
Näf et al. "The Four Isomeric 1,3,5–Undercatrienes. Synthesis and Configurations Assignment" Helvitica Chimica Acta vol. 58 (1975) pp. 1016–1037.
Boland et al. "(Z)–Selektive Recuktion von konjugierten Drieifachbindugen mit Zn $(Cu.Ag)^{1)}$" J. Prakt. Chem. vol. 336 (1994) pp. 714–715.

* cited by examiner

CATALYTIC REDUCTION OF ALKYNE COMPOUNDS

The present invention relates to a novel process for the reduction of alkyne compounds; in particular, the invention relates to a process for the preparation of cyclohexene derivatives which are suitable as intermediates for the preparation of carotinoids.

A large number of the industrial carotinoid syntheses described in the literature, including the preparation of astaxanthine, proceed via cyclohexene intermediates which, in additon to one or more C=C double bonds, also contain a C=C triple bond. To form a conjugated double bond system, this triple bond has to be partially reduced in a separate process step.

In the case of the alkynediol IVa involved in the astaxanthine synthesis described in DE-A-43 22 277, this can be done with zinc/acetic acid in methylene chloride.

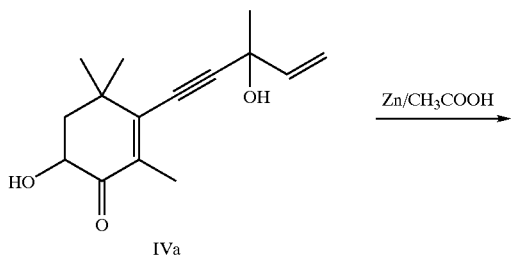

IVa

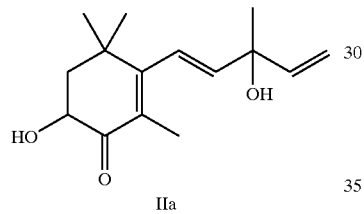

IIa

EP-A-0 005 748 relates to another process for the preparation of astaxanthine, in which the partial reduction of the alkynediol of formula IIIa is likewise carried out with zinc/acetic acid in methylene chloride.

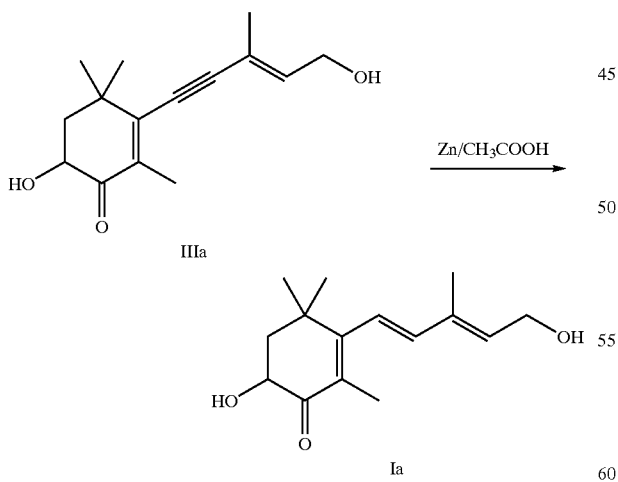

IIIa

Ia

The disadvantage of the zinc/acetic acid reduction described is the inadequate selectivity of the method. Unwanted by-products, e.g. the formation of spiro compounds which cannot be converted to the desired secondary products later in the synthesis, can lead to significant losses of yield.

Other methods of reduction are described inter alia in J. Amer. Oil Chem. Soc. 49 (1972) 72, where the reduction of triple bonds to cis double bonds in long-chain conjugated fatty acids is carried out with zinc in boiling protic solvents.

The drastic reduction conditions mentioned here are unsuitable for thermally labile compounds.

Helv. Chim. Acta 58 (1975) 1016 describes the reduction of conjugated alkynes in protic solvents. The reducing agent used by the authors is zinc dust which has been activated by the addition of potassium cyanide.

On the one hand, the abovementioned methods give only moderate yields; on the other hand, the activation with potassium cyanide carries an appreciable health risk.

The paper published in Journal für praktische Chemie 336 (1994) 714–715 contains a method for the (Z)-selective reduction of conjugated triple bonds with a combination of Zn (Cu/Ag) in polar protic solvents, e.g. methanol/water.

This process has the disadvantage that the reagent is very expensive to prepare and moreover must always be freshly prepared.

It is therefore an object of the present invention to provide a process for the partial reduction of alkyne compounds which avoids the abovementioned disadvantages of the prior art.

We have found that this object is achieved by a process for the preparation of cyclohexene derivatives of general formulae I or II:

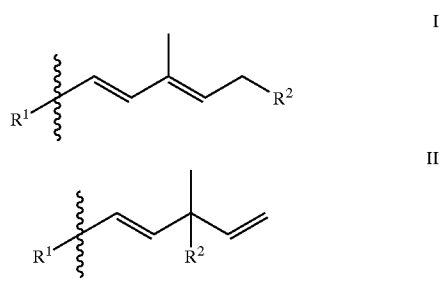

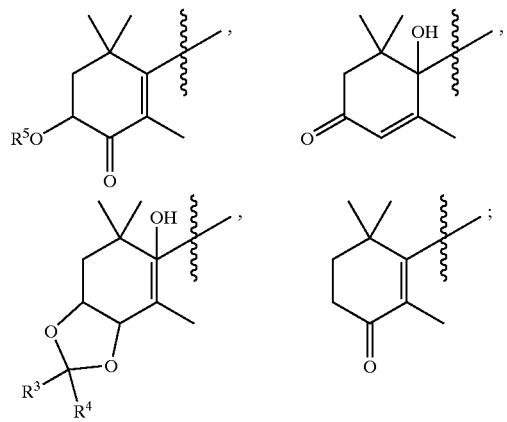

in which the substituents $R^1$ and $R^2$ independently of one another are defined as follows:

$R^1$ is $R^2$ is OH or a protective group convertible to a hydroxyl group by hydrolysis;

$R^3$ and $R^4$ are hydrogen or $C_1$–$C_4$-alkyl; and $R^5$ is hydrogen or $C_1$–$C_4$-acyl, by the reduction of alkyne compounds of general formulae III or IV:

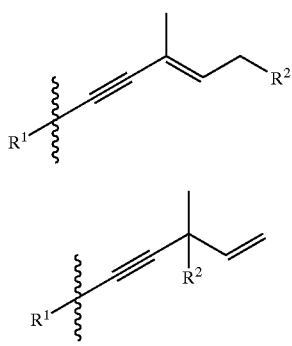

in which the substituents $R^1$ and $R^2$ are as defined above, wherein the reducing agent used is a mixture of zinc and at least one compound B selected from the group consisting of ammonium salts, copper salts and alkali metal and alkaline earth metal salts.

Alkyl radicals $R^3$ and $R^4$ which may be mentioned are linear or branched $C_1$–$C_4$-alkyl chains, e.g. methyl, ethyl, n-propyl, 1-methylethyl, n-butyl, 1-methylpropyl, 2-methylpropyl and 1,1-dimethylethyl. Preferred alkyl radicals are methyl and ethyl.

The radicals $R^3$ and $R^4$ can also form a cycloheptyl or cyclohexyl ring together with the carbon atom to which they are bonded.

Substituents $R^5$ which may be mentioned are linear or branched $C_1$–$C_4$-acyl chains, e.g. formyl, acetyl, propionyl and isopropionyl. The preferred acyl radical is acetyl.

Suitable protective groups $R^2$ convertible to a hydroxyl group by hydrolysis are functional groups which can be converted to the hydroxyl group relatively easily. Examples which may be mentioned are ether groups such as

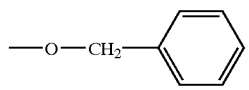

and —O—C(CH$_3$)$_3$
silyl ether groups such as —O—Si(CH$_3$)$_3$, —O—Si(CH$_2$CH$_3$)$_3$, —O—Si(isopropyl)$_3$, —O—Si(CH$_3$)$_2$(tert-butyl) and —O—Si(CH$_3$)$_2$(n-hexyl), or substituted methyl ether groups such as the α-alkoxyalkyl ether groups of the formulae —O—CH$_2$—O—CH$_3$,

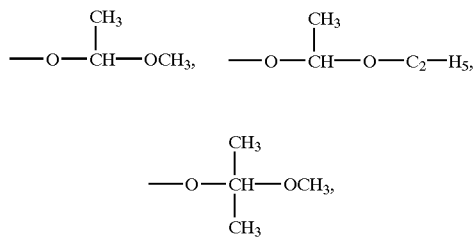

and suitable pyranyl ether groups such as the tetrahydropyranyloxy group and the 4-methyl-5,6-dihydro-2H-pyranyloxy group.

The group used for $R^2$ is particularly advantageously the tetrahydropyranyloxy group:

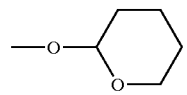

or the α-ethoxyethoxy group of the formula

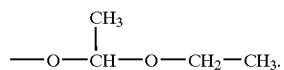

Conditions for cleaving the abovementioned protective groups can be found inter alia in T. Greene "Protective Groups in Organic Chemistry", John Wiley & Sons, 1981, Chapter 2.

In one preferred process variant, the reducing agent used is a mixture of zinc and at least one ammonium salt of formula V:

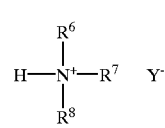

in which the substituents independently of one another are defined as follows:
$R^6$ to $R^8$
are hydrogen, $C_1$–$C_6$-alkyl or aryl; and
$Y^-$ is an anion of an organic or inorganic acid.

Alkyl radicals $R^6$ to $R^8$ which may be mentioned are linear or branched $C_1$–$C_6$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Preferred alkyl radicals are methyl, ethyl, n-propyl and 1-methylethyl.

Hydrogen may be mentioned as the particularly preferred radical for $R^6$ to $R^8$.

Aryl is to be understood as meaning aromatic rings or ring systems having from 6 to 18 carbon atoms in the ring system, for example phenyl or naphthyl, which can optionally be substituted by one or more radicals such as halogen, e.g. fluorine, chlorine or bromine, amino, $C_1$–$C_4$-alkylamino, $C_1$–$C_4$-dialkylamino, hydroxyl, $C_1$–$C_4$-alkyl, $C_1$–$C_4$-alkoxy or other radicals. Optionally substituted phenyl, methoxyphenyl and naphthyl are preferred.

$Y^-$ is generally an anion of an organic or inorganic acid.

Organic acids are to be understood as meaning, inter alia, aliphatic and aromatic carboxylic acids, for example benzoic acid or $C_1$–$C_{12}$-alkanoic acids, preferably $C_1$–$C_6$-alkanoic acids such as formic acid, acetic acid, propionic acid, butyric acid or caproic acid, particularly preferably acetic acid, or dicarboxylic acids such as oxalic acid, malonic acid or succinic acid.

$Y^-$ can also be an anion of an organic sulfonic acid, such as methanesulfonate or para-toluenesulfonate.

Examples of inorganic acids are, inter alia, hydrochloric acid, hydrobromic acid, carbonic acid, sulfuric acid, sulfurous acid, nitric acid, nitrous acid and phosphoric acid.

The present invention further relates to a process for the preparation of cyclohexene derivatives of formulae I or II wherein the reducing agent used is a mixture of zinc and at least one copper salt selected from the group consisting of copper(I) bromide, copper(I) chloride, copper(II) acetate, copper(II) bromide, copper(II) carbonate, copper(II) chloride, copper(II) nitrate, copper(II) oxalate and copper (II) sulfate. Copper(II) sulfate may be mentioned as the preferred copper salt.

In another embodiment of the process according to the invention, the reducing agent used is a mixture of zinc and at least one alkali metal or alkaline earth metal salt selected from the group consisting of sodium bromide, sodium chloride, sodium acetate, sodium carbonate, sodium hydrogencarbonate, sodium oxalate, sodium sulfate, potassium bromide, potassium chloride, potassium acetate, potassium carbonate, potassium hydrogencarbonate, potassium oxalate, potassium sulfate and the corresponding lithium salts, calcium bromide, calcium chloride, calcium acetate, calcium carbonate, calcium oxalate, calcium sulfate, magnesium bromide, magnesium chloride, magnesium acetate, magnesium carbonate, magnesium oxalate and magnesium sulfate and the corresponding barium salts.

In one particularly preferred process variant, the reducing agent used is a mixture of zinc and at least one ammonium salt of formula V selected from the group consisting of ammonium chloride, ammonium carbonate, ammonium hydrogencarbonate, ammonium sulfate and ammonium acetate. The substituents $R^6$ to $R^8$ are all hydrogen in this case. Ammonium chloride may be mentioned as the very particularly preferred ammonium salt.

The process according to the invention is particularly suitable for the preparation of the cyclohexene compounds of formulae Ia and IIa:

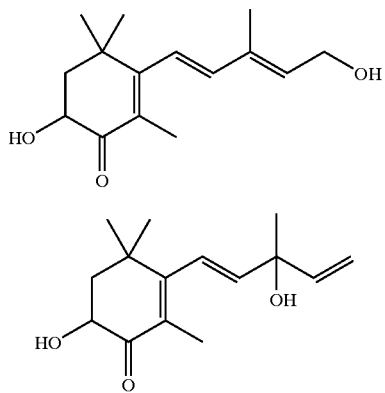

The general procedure for carrying out the process is to meter an aqueous solution of the compound B into the alkyne compounds of formulae III or IV and then to add the zinc to this mixture, or to meter a suspension of zinc in an aqueous solution of the compound B into the abovementioned alkyne compounds.

However, the converse procedure is also possible, the zinc being suspended in an aqueous solution of the compound B and the alkyne compounds III or IV being added to this suspension.

It has furthermore been found that the reduction according to the invention takes place particularly advantageously in the presence of water.

The amount of water is chosen so that the compound B is dissolved or partially dissolved. Normally 15 to 500 ml of water, preferably 20 to 400 ml and particularly preferably 30 to 250 ml of water are used per mole of zinc.

The addition of an inert solvent has also proved advantageous for the progress of the reduction.

In general, any solvents inert toward the compounds I to IV are suitable as inert solvents in the process according to the invention. The process is preferably carried out in chlorohydrocarbons, e.g. dichloromethane, perchloroethylene or chloroform, or in an ether solvent such as a dialkyl ether, tetrahydrofuran or dioxane, and especially in the water-immiscible methyl tert-butyl ether. Other suitable solvents are aromatic hydrocarbons, especially toluene, and $C_1$–$C_3$-alcohols such as methanol, ethanol or propanol.

It is preferred to use a 10 to 50% by weight solution of the alkynediol in one of the abovementioned solvents, particularly preferably a 15 to 30% by weight solution of the alkynediol in methylene chloride.

In addition to the abovementioned solvents, it is also possible to use acetic acid as a cosolvent.

When using the zinc/copper reducing agent system, said reducing agent is prepared by adding approx. 0.02 mol of the abovementioned copper salts, especially copper sulfate, in aqueous solution per mole of zinc.

The zinc is used in an amount of about 0.5 to 5, preferably 0.7 to 3, particularly preferably 1 to 2 and very particularly preferably 1.2 to 1.6 gram atoms per mole of alkynediol to be reduced. The zinc can be metered in one or more portions.

0.5 to 5 mol, preferably 0.7 to 3 mol and particularly preferably 1 to 2 mol of compound B are used per mole of zinc.

The reduction can be carried out at temperatures between 0° C. and the boiling point of the particular solvent. Preferred reaction temperatures range from 10 to 80° C. and particularly preferably from 35 to 45° C.

The subject of the present invention will be illustrated in greater detail by means of the following examples.

Example 1

100 g (0.4 mol) of 92% pure 6-hydroxy-3-(3-hydroxy-3-methyl-4-penten-1-ynyl)-2,4,4-trimethyl-2-cyclohexen-1-one of formula IVa were dissolved in 400 ml of methylene chloride and mixed with a solution of 28.7 g (0.54 mol) of ammonium chloride in 100 ml of water. The mixture was cooled to 10° C., 35.2 g (0.54 mol) of zinc powder were added and the resulting mixture was stirred for 2 hours without additional cooling. The reaction mixture was then heated to the reflux point (36–40° C.) and stirred for a further 3 hours at this temperature. After cooling to 10° C., the residue was filtered off and washed with 2×100 ml of methylene chloride. The mother liquor and the washing filtrate were combined and extracted by shaking with 200 ml of water. After distillation of the solvent, an oily residue was obtained which, according to gas chromatographic analysis, contained 78.1 GC area % of alkenediol of formula IIa and 3.3 GC area % of alkynediol of formula IVa.

Example 2

A solution of 100 g (0.4 mol) of alkynediol of formula IVa (purity: 92%) in 200 ml of methylene chloride was added dropwise over 2 hours at 25° C., with stirring, to a suspension of 28.7 g (0.54 mol) of ammonium chloride and 35.2 g (0.54 mol) of zinc powder in 100 ml of water. When the dropwise addition had ended, the mixture was heated to 35° C. and stirred for 18 hours at 35° C. A determination of content by gas chromatography showed 77.36 GC area % of alkenediol (formula IIa) and 12.95 GC area % of alkynediol (formula IVa). After the addition of a further 5.74 g (0.11 mol) of ammonium chloride dissolved in 20 ml of water, and 7 g (0.11 mol) of zinc powder, the reaction was continued for 2 hours at 35° C. and an analysis of content by gas chromatography showed 87.9 GC area % of alkenediol (formula IIa) and <1 GC area % of alkynediol (formula IVa).

Example 3

100 g (0.4 mol) of alkynediol of formula IVa (purity: 92%) were dissolved in 400 ml of methylene chloride. 28.7 g (0.54 mol) of ammonium chloride and 35.2 g (0.54 mol) of zinc powder were introduced successively, with stirring. 25 ml of water were added at room temperature and the mixture was stirred under reflux (38–40° C.) for 12 hours. After work-up, a residue was obtained which, according to gas chromatographic analysis, contained 81.2 GC area % of alkenediol of formula IIa and 3.3 GC area % of alkynediol of formula IVa.

Example 4

100 g (0.4 mol) of alkynediol of formula IVa (92% pure) were dissolved in 400 ml of methylene chloride and added to a solution of 51.8 g (0.54 mol) of ammonium carbonate dissolved in 100 ml of water. 35.2 g (0.54 mol) of zinc powder were then introduced. The mixture was heated to 36–38° C., with stirring, during which a violent evolution of $CO_2$ took place. After a stirring time of 12 hours at a temperature of 36–38° C., a sample was analyzed by GC: alkenediol content: 73.87 GC area %; alkynediol content: 4 GC area %.

Example 5 a) Preparation of the Zn/Cu reducing agent (according to DRP 84891)

100 g of Zn powder were suspended in 150 ml of demineralized water, and 4 g of copper sulfate were introduced at room temperature (–25° C.), with thorough stirring. Stirring is continued until the blue coloration in the suspension has disappeared. After a further 1 hour of stirring, the solid is filtered off with suction and washed with demineralized water, the moist product weighing 131 g.

b) Reduction of the alkynediol with Zn/Cu 100 g (0.4 mol) of alkynediol of formula IVa were dissolved in 400 ml of methylene chloride. 46.3 g (approx. 0.54 mol) of the moist Zn/Cu reducing agent prepared under a) were suspended in 100 ml of water and introduced into the alkynediol/methylene chloride solution. After the reducing agent had been added, the mixture was heated to 36° C. After a stirring time of 6 hours, a GC analysis was performed 78.4 GC area % of alkenediol (formula IIa) and 9.7 GC area % of alkynediol (formula IVa).

Example 6 (Comparative Example)

100 g (0.4 mol) of alkynediol of formula IVa (92% pure) were dissolved in 400 ml of methylene chloride. 80 ml of acetic acid ere added at 0° C. and a total of 35.2 g (0.54 mol) of zinc powder were introduced in eight 4.4 g portions at 15 minute intervals. After a stirring time of 45 min at 0°, zinc acetate was filtered off with suction and washed with methylene chloride until free of useful product. After work-up the filtrate was analyzed by GC and contained 62 GC area % of alkenediol of formula IIa and 21 GC area % of spiro compound of formula VI.

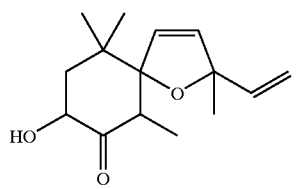

We claim:

1. A process for the preparation of cyclohexene derivatives of general formulae I or II:

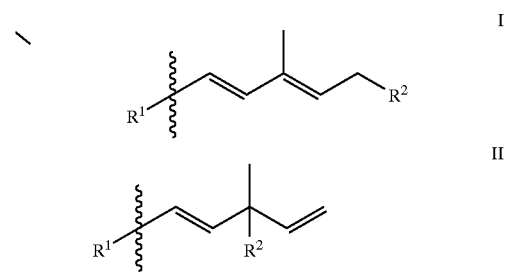

in which the substituents $R^1$ and $R^2$ independently of one another are defined as follows:

$R^1$ is

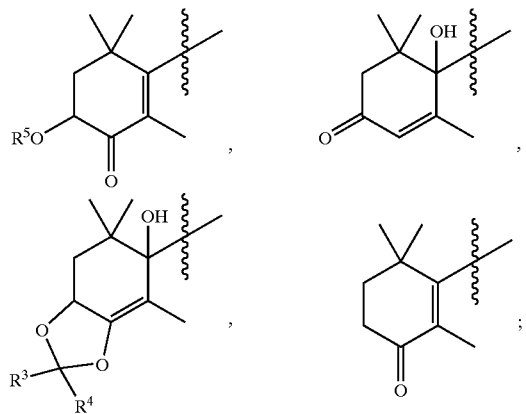

$R^2$ is OH or a protective group convertible to a hydroxyl group by hydrolysis;

$R^3$ and $R^4$ are hydrogen or $C_1$–$C_4$-alkyl; and $R^5$ is hydrogen or $C_1$–$C_4$-acyl, by the reduction of alkyne compounds of general formulae III or IV:

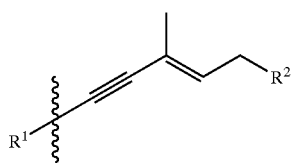

-continued

IV

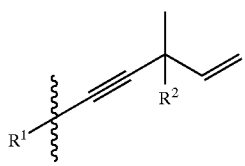

in which the substituents $R^1$ and $R^2$ are as defined above, wherein the reducing agent used is a mixture of zinc and at least one compound B selected from the group consisting of ammonium salts, copper salts and alkali metal and alkaline earth metal salts.

2. A process as claimed in claim 1 wherein the reducing agent used is a mixture of zinc and at least one ammonium salt of formula V:

V

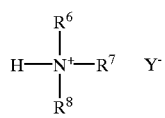

in which the substituents independently of one another are defined as follows:

$R^6$ to $R^8$
are hydrogen, $C_1$–$C_6$-alkyl or aryl; and
$Y^-$ is an anion of an organic or inorganic acid.

3. A process as claimed in claim 2 wherein the reducing agent used is a mixture of zinc and at least one ammonium salt selected from the group consisting of ammonium chloride, ammonium carbonate, ammonium hydrogencarbonate, ammonium sulfate and ammonium acetate.

4. A process as claimed in claim 1 wherein the reducing agent used is a mixture of zinc and at least one copper salt selected from the group consisting of copper(I) bromide, copper(I) chloride, copper(II) acetate, copper(II) bromide, copper(II) carbonate, copper(II) chloride, copper(II) nitrate, copper(II) oxalate and copper(II) sulfate.

5. A process as claimed in claim 1 wherein the reduction is carried out in the presence of water.

6. A process as claimed in claim 1 wherein the reduction is carried out in an organic solvent inert toward the cyclohexene derivatives of general formulae I to IV.

7. A process as claimed in claim 1 for the preparation of cyclohexene compounds of formulae Ia and IIa Ia

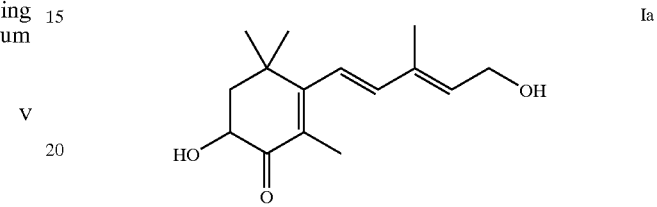

IIa

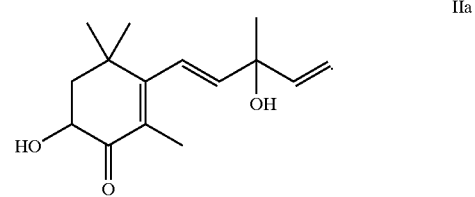

* * * * *